(12) United States Patent
Reaney

(10) Patent No.: US 6,409,649 B1
(45) Date of Patent: Jun. 25, 2002

(54) METHOD FOR COMMERCIAL PREPARATION OF CONJUGATED LINOLEIC ACID USING RECYCLED ALKALI TRANSESTERIFICATION CATALYST

(75) Inventor: Martin J. T. Reaney, Saskatoon (CA)

(73) Assignee: Her Majesty the Queen in right of Canada, as represented by the Minister of Agriculture & Agri-Food Canada, Ottawa (CA)

(*) Notice: Subject to any disclaimer, the term of this patent is extended or adjusted under 35 U.S.C. 154(b) by 0 days.

(21) Appl. No.: 09/994,061

(22) Filed: Nov. 27, 2001

(51) Int. Cl.$^7$ ................................................ C07B 35/08
(52) U.S. Cl. ........................................................ 584/126
(58) Field of Search ............................................ 554/126

(56) References Cited

U.S. PATENT DOCUMENTS

| | | |
|---|---|---|
| 2,242,230 A | 5/1941 | Burr |
| 2,343,644 A | 3/1944 | Cawley |
| 2,350,583 A | 6/1944 | Bradley |
| 2,389,260 A | 11/1945 | Kirschenbauer |
| 4,164,505 A | 8/1979 | Krajca |
| 4,376,711 A | 3/1983 | Shaub |
| 4,381,264 A | 4/1983 | Struve |
| 4,393,043 A | 7/1983 | Koulbanis |
| 5,053,534 A | 10/1991 | Cosgrove |
| 5,070,104 A | 12/1991 | Pariza |
| 5,194,640 A | 3/1993 | Cosgrove |
| 5,428,072 A | 6/1995 | Cook |
| 5,430,066 A | 7/1995 | Cook |
| 5,504,114 A | 4/1996 | Cook |
| 5,554,646 A | 9/1996 | Cook |
| 5,585,400 A | 12/1996 | Cook |
| 5,674,901 A | 10/1997 | Cook |
| 5,760,083 A | 6/1998 | Cook |
| 5,770,217 A | 6/1998 | Kutilek |
| 5,892,074 A | 4/1999 | Seidel |
| 5,986,116 A * | 11/1999 | Iwata et al. .................. 554/126 |

OTHER PUBLICATIONS

Soap in Oil Titrimetric Method, AOCS Recommended Practice Cc 17–95.
Free Fatty Acids, AOCCS Official Method Ca 5a–40.
Drying Oils and Resins, Industrial and Engineering Chemistry, pp237–242, Feb. 1942.

* cited by examiner

Primary Examiner—Deborah D. Carr
(74) Attorney, Agent, or Firm—Dowell & Dowell, P.C.

(57) ABSTRACT

Conjugated linoleic acid is readily prepared by mixing crude alkaline glycerol solution derived as a byproduct of triglyceride transesterification and a linoleate rich triglyceride, ester, soap, phospholipid, fatty acid, or wax and heating the mixture sufficiently to conjugate the linoleate double bonds. The reaction produces a favorable isomer mixture enriched in 10,12-trans,cis octadecadienoic and 9,11-cis,trans-octadecadienoic acids.

20 Claims, No Drawings

METHOD FOR COMMERCIAL PREPARATION OF CONJUGATED LINOLEIC ACID USING RECYCLED ALKALI TRANSESTERIFICATION CATALYST

FIELD OF INVENTION

This invention relates to an improved process for preparation of conjugated linoleic acid (CLA) that overcomes the high input cost of alkali and solvent by recycling alkali and glycerol mixtures derived from triglyceride transesterification. Surprisingly, the alkali in the recycled solutions supports a vigorous reaction and the crude nature of the mixture does not contribute to undesirable colours in the CLA produced using these products.

BACKGROUND OF THE INVENTION

Conjugated linoleic acid is the trivial name given to a series of eighteen carbon diene fatty acids with conjugated double bonds. Applications of conjugated linoleic acid vary from treatment of medical conditions such as anorexia (U.S. Pat. No. 5,430,066) and low immunity (U.S. Pat. No. 5,674,901) to applications in the field of dietetics where CLA has been reported to reduce body fat (U.S. Pat. No. 5,554,646) and to inclusion in cosmetic formulae (U.S. Pat. No. 4,393,043).

CLA shows similar activity in veterinary applications. In addition, CLA has proven effective in reducing valgus and varus deformity in poultry (U.S. Pat. No. 5,760,083), and attenuating allergic responses (U.S. Pat. No. 5,585,400). CLA has also been reported to increase feed conversion efficiency in animals (U.S. Pat. No. 5,428,072). CLA-containing bait can reduce the fertility of scavenger bird species such as crows and magpies (U.S. Pat. No. 5,504,114).

Industrial applications for CLA also exist where it is used as a lubricant constituent (U.S. Pat. No. 4,376,711). CLA synthesis can be used as a means to chemically modify linoleic acid so that it is readily reactive to Diels-Alder reagents (U.S. Pat. No. 5,053,534). In one method linoleic acid was separated from oleic acid by first conjugation, then reaction with maleic anhydride followed by distillation (U.S. Pat. No. 5,194,640).

Conjugated linoleic acid occurs naturally in ruminant depot fats. The predominant form of CLA in ruminant fat is the cis,trans-9,11-octadecadienoic acid which is synthesized from linoleic acid in the rumen by micro-organisms like *Butryvibrio fibrisolvens*. The level of CLA found in ruminant fat is in part a function of dietary cis,cis-9,12-octadecadienoic acid and the level of CLA in ruminant milk and depot fat may be increased marginally by feeding linoleic acid (U.S. Pat. No. 5,770,247).

CLA may also be prepared by any of several analytical and preparative methods. Pariza and Ha pasteurized a mixture of butter oil and whey protein at 85° C. for 5 minutes and noted elevated levels of CLA in the oil (U.S. Pat. No. 5,070,104). CLA produced by this mechanism is predominantly a mixture of cis,trans-9,11-octadecadienoic acid and trans,cis-10,12-octadecadienoic acid.

CLA has also been produced by the reaction of soaps with strong alkali bases in molten soaps, alcohol, and ethylene glycol monomethyl ether (U.S. Pat. Nos. 2,389,260, 2,242,230 & 2,343,644). These reactions are inefficient as they require the multiple steps of formation of the fatty acid followed by production of soap from the fatty acids, and subsequently increasing the temperature to isomerize the linoleic soap. The CLA product is generated by acidification with a strong acid (sulfuric or hydrochloric acid) and repeatedly washing the product with brine or $CaCl_2$.

CLA has been synthesized from fatty acids using $SO_2$ in the presence of a sub-stoichiometric amount of soap forming base (U.S. Pat. No. 4,381,264). The reaction with this catalyst produced predominantly the all trans configuration of CLA.

Efficient synthesis of cis,trans-9,11-octadecadienoic from ricinoleic acid has been achieved (U.S. Pat. No. 5,892,074). This synthesis, although efficient, uses expensive elimination reagents such as 1,8-diazobicyclo-(5,4,0)-undecene. For most applications the cost of the elimination reagent increases the production cost beyond the level at which commercial production of CLA is economically viable.

Water may be used in place of alcohols in the production of CLA by alkali isomerization of soaps (U.S. Pat. Nos. 2,350,583, 4,164,505). When water is used for this reaction it is necessary to perform the reaction in a pressure vessel whether in a batch (U.S. Pat. No. 2,350,583) or continuous mode of operation (U.S. Pat. No. 4,164,509). The process for synthesis of CLA from soaps dissolved in water still requires a complex series of reaction steps. Bradley and Richardson (*Industrial and Engineering Chemistry* February 1942 vol 34 no2 237–242) were able to produce CLA directly from soybean triglycerides by mixing sodium hydroxide, water and oil in a pressure vessel. Their method eliminated the need to synthesize fatty acids and then form soaps prior to the isomerization reaction. However, they reported that they were able to produce an oil with up to 40 percent CLA. Quantitative conversion of the linoleic acid in soybean oil to CLA would have produced an fatty acid mixture with approximately 54 percent CLA.

Commercial conjugated linoleic acid often contains a mixture of positional isomers that may include trans,cis-8,10-octadecadienoic acid, cis,trans-9,11-octadecadienoic acid, trans,cis-10,12-octadecadienoic acid, and cis,trans-11,13-octadecadienoic acid (Christie, W. W., G. Dobson, and F. D. Gunstone, (1997) Isomers in commercial samples of conjugated linoleic acid. J. Am. Oil Chem. Soc. 74, 11, 1231).

OBJECT OF INVENTION

The present invention relates to a method of production of CLA using vegetable oils, esters, fatty acids or soaps that are rich in linoleate moieties. The method uses alkali, formerly used for triglyceride transesterification, for conversion of the soaps in the soapstock to conjugated linoleate soaps. The method also uses crude glycerol derived from triglyceride transesterification as the solvent for CLA production. After the conjugation reaction the soaps may be extracted with acid to yield conjugated linoleic acid or with salts to yield soaps.

BRIEF STATEMENT OF INVENTION

By one aspect of this invention there is provided a process for producing conjugated linoleic acid from a material rich in linoleate moieties comprising; mixing said material with a waste alkaline glycerol derived from alkali transesterification of triglycerides, heating to a temperature above 170° C., cooling and separating said conjugated linoleic acid by the addition of at least one of the group consisting of a salt, a salt solution and an acid.

DETAILED DESCRIPTION OF THE PREFERRED EMBODIMENTS

The process of the present invention quantitatively converts oils, soapstocks, fatty acids, soaps and esters rich in linoleate moieties to conjugated linoleic acid by reacting the same in a crude alkaline glycerol solution. The process is novel in that the crude alkali glycerol solution is prepared as a by-product of alkaline transesterification of triglycerides with a lower alcohol. Surprisingly, the recycled alkaline solution has sufficient reactivity to isomerize linoleate to conjugated linoleate moieties. The oils, soapstocks, fatty acids, soaps and esters may be added to the alkaline glycerol solution directly. However, as a unique embodiment of this invention the alkaline glycerol solution may be also used as a refining agent that extracts fatty acids from vegetable oils.

The conversion of linoleate moieties in vegetable oils, fatty acids, esters, soapstocks and soaps to conjugated linoleates is achieved by mixing the linoleate containing material with the alkaline glycerol solution and increasing the temperature to above 170° C. The vegetable oil, soaps, fatty acids, esters and soapstocks used may be derived from cottonseed, cucumber, grape seed, corn, safflower, soybean, sunflower or walnut or any other oil, wax or ester that is rich in linoleate. The reaction may proceed with the alkali present in the glycerol solution alone but additional alkali such as sodium metal, sodium hydroxide, sodium alkoxylate, potassium metal, potassium hydroxide or potassium alkoxylate or solutions thereof may be added to augment the reaction. The reaction proceeds at temperatures above 170° C. and the reaction accelerates with increases in temperature. Preferred embodiments involve performing the reaction above 180° C. As the reaction mixture may contain water or residual alcohol from transesterification it may be necessary to confine the reaction in a sealed pressure vessel.

In another embodiment the alkaline glycerol may be used to refine a vegetable oil or ester that is rich in the free fatty acid linoleic acid. Once the fatty acid present in the oil is converted to its soap, it becomes soluble in the glycerol solution. The oil is said to be refined with the removal of fatty acids and at the same time an alkali glycerol solution is produced that contains the desired linoleate required for CLA synthesis. The conversion of linoleate moieties to conjugated linoleates is achieved by increasing the temperature to above 170° C. The vegetable oil refined by glycerol could include flaxseed, cottonseed, cucumber, grape seed, corn, safflower, soybean, sunflower or walnut or any other oil, wax or ester that is rich in linoleate. The reaction may proceed with the alkali alone present in the glycerol solution but additional alkali such as sodium metal, sodium hydroxide, sodium alkoxylate, potassium metal, potassium hydroxide or potassium alkoxylate or solutions thereof may be added to augment the reaction. The reaction proceeds at temperatures above 170° C. and the reaction accelerates with increases in temperature. Preferred embodiments involve performing the reaction above 180° C. As the reaction mixture may contain water or residual alcohol from transesterification it may be necessary to confine the reaction in a sealed pressure vessel.

The reaction proceeds very rapidly at temperatures above 190° C. and is sensitive to small changes in temperature. The reaction vessel used for the process must establish a homogeneous temperature or the reaction will not proceed uniformly. Homogeneous temperature is achieved by vigorous stirring or turbulent flow conditions. In a preferred embodiment safflower oil is added to alkaline glycerol solution and the solution is heated to 200° C. for 2 h. Conjugated linoleic acid is liberated from the solution by cooling the mixture to between 20 and 150° C. and adding acid. The glycerol separated by this method is readily recovered and refined. It is preferred to bring the pH of the contents of the reactor to pH 4 or lower through the addition of either a mineral or organic acid. Acids that may be used include, but are not limited to, hydrochloric acid, sulfuric acid, phosphoric acid and citric acid. It is found that the use of sulfuric and hydrochloric acid is problematic in that these strong acids may react chemically with the CLA during separation. The preferred embodiment of this invention involves the use of phosphoric or citric acid to hydrolyse the soaps. When phosphoric acid is used the waste solution can be neutralized and used as a surface applied fertilizer and there are no disposal costs for discarding this product.

Reaction progress was determined by gas liquid chromatography of the free fatty acids using a J&W DB-FFAP column (30 M by 0.32 micrometer ID, coating thickness 0.25 micrometer).

EXAMPLES

Example 1

Transesterification of a Triglyceride with Potassium Hydroxide and Preparation of the Alkaline Glycerol Solution Two hundred grams of potassium hydroxide were dissolved in 2,200 grams of methanol in a four-liter glass beaker. Half of the mixture (1,200 g) was added with agitation to 10 kg of refined safflower oil in a 20 L polyethylene plastic pail. The contents of the pot were stirred with an overhead agitator for 2 hours and then agitation was stopped and the contents of the pot were allowed to settle for 12 hours. After settling, the contents separated into an upper layer mainly comprised of methyl ester and a lower layer comprised of methanol, glycerol and residual alkali. The methyl ester layer was decanted into a second stainless steel pot and the other half of the mixture of methanol and potassium hydroxide were added to the second pot with agitation. The material from the bottom of the first pot was poured into a 4 L glass separating funnel and allowed to settle for an additional hour. The bottom layer of alkali solution in the separatory funnel was saved and the upper layer of ester was returned to the second pot for continued reaction. The second pot was stirred for an additional 2 hours and then allowed to settle overnight. After settling the upper layer was decanted and the bottom layer was placed in a separating funnel. The bottom layer of glycerol, alkali, soaps and methanol was mixed with the bottom layer from the first reaction. The combined layers were placed into a rotary evaporator flask and residual solvent was removed under vacuum. To produce sufficient recycled alkaline glyderol for the remaining experiments the procedure of producing methyl esters was repeated three times and the crude alkaline glycerol layers were pooled and used for the further examples.

Example 2

Conversion of Safflower Oil Linoleate to Conjugated Linoleate Using Alkaline Glycerol from Transesterification Six hundred grams of crude alkaline glycerol prepared as described in example 1 were mixed with 300 grams of safflower oil in a 1 L beaker. The contents of the beaker were stirred and heated with a temperature controlled magnetic stirring hotplate. The contents of the beaker were heated to 200° C. for 3 hours and the disappearance of linoleate and appearance on conjugated linoleate was determined by GLC. After 3 hours 95% of the linoleate was converted to conjugated linoleate isomers.

Example 3
Refining Safflower Oil with the Alkaline Glycerol Solution and Conversion of Extracted Linoleate to Conjugated Linoleate Twenty liters of unrefined cold-pressed safflower oil containing 0.2% free fatty acids were heated to 80° C. in a stainless steel pot and mixed with 500 g of crude alkaline glycerol prepared as described in example 1. The mixture was stirred vigorously for 20 minutes then allowed to settle for 4 hours. After four hours the upper layer of refined safflower oil was found to have a FFA concentration of 0% and soap level of <5 ppm as determined by AOCS methods Ca 5a and Cc 17–95 respectively.

The lower layer was removed from the beaker and placed into 200 mL centrifuge bottles which were placed in a swing out rotor and centrifuged at 1000×g for 3 minutes after which an upper layer of oil was decanted. The lower layer was found to be 14% soaps on a dry weight basis and these soaps were primarily potassium linoleate. Four hundred grams of the lower layer was then heated to 200° C. for 3 hours to effect the conversion of linoleate soaps to conjugated linoleate soaps.

After 3 hours the reaction mixture was cooled to 100° C. and phosphoric acid was added slowly until a pH of 3.0 was achieved. After acidification agitation and heating were ended and the contents of the beaker separated into two distinct layers. The upper layer was found to be a 94% solution of fatty acids predominantly composed of conjugated isomers of linoleic acid. The lower layer of the reaction mixture contained glycerol and dissolved salts.

Example 4
Extraction of Linoleate as a Calcium Soap by the Addition of a Calcium Salt The calcium soap of linoleic acid was produced by reacting 600 g of the crude alkali glycerol with 300 g of oil as described in example 2. After cooling the reaction mixture to 100° C., as described in example 2, the potassium soaps were converted to calcium soaps by adding 100 g of anhydrous calcium chloride to the reaction mixture. The addition of the calcium salt converted the entire contents of the beaker into a gummy mass. The mass was transferred to a Waring blender and 1 L of deionized water was added to the blender. The contents of the blender were homogenized for 60 seconds on a low setting and the contents of the blender were placed on a Tyler 100 mesh screen. A coarse fraction of calcium soaps was retained on the screen. A small amount of fine fraction and reaction solution passed through the screen. The coarse fraction was returned to the blender and 1 L of water was added. The contents of the blender were again homogenized for 60 seconds at a low setting and passed over a Tyler 100 mesh screen. Using this method the soaps were washed twice more with 1 L of water to remove residual glycerol. The fine fraction was recovered by centrifugation and decanting the upper layer and drying the fines in the oven.

Example 5
Extraction of Linoleate as a Sodium Soap by the Addition of Sodium Chloride The sodium soap of linoleic acid was produced by reacting 600 g of the crude alkali glycerol with 300 g of oil as described in example 2. After cooling the reaction to 100° C., as described in example 2, 1 L of a saturated sodium chloride was added to the reaction mixture. The reaction mixture was centrifuged at 2,000×g for 5 minutes to separate the products into two layers. The lower layer was withdrawn and the upper layer was washed a second and third time with 1 L of saturated sodium chloride solution. The thrice washed sodium soaps formed a coarse soapy solid which was dried under vacuum.

Example 6
Extraction of Linoleate as a Fatty Acid by the Addition of Phosphoric Acid The potassium soap of linoleic acid was produced by reacting 600 g of the crude alkali glycerol with 300 g of oil as described in example 2. After 3 hours the reaction mixture was cooled to 100° C. and phosphoric acid was added slowly until a pH of 3.0 was achieved. After acidification agitation and heating were ended and the contents of the beaker separated into two distinct layers. The upper layer was found to be a 94% solution of fatty acids predominantly composed of conjugated isomers of linoleic acid. The lower layer of the reaction mixture contained glycerol and dissolved salts.

Example 7
No Reaction Occurs if Glycerol and Oil are Mixed and Heated to 200° C.

To demonstrate that the residual alkali in the glycerol is required to convert the linoleate in the oil to conjugated forms a counter-example was performed. Six hundred grams of alkali-free U.S.P glycerol and 300 g of vegetable oil were added to a 1000 mL beaker. The beaker was heated and stirred vigorously as described in example 2. No chemical reaction occurred and no CLA was formed.

Example 8
No Reaction when Insufficient Alkali is Present

All conditions are the same as in example 2 except that 500 mL of vegetable oil was added instead of 300 mL. Under these conditions no reaction took place.

Example 9
Supplemental Addition of Catalyst Restores Reaction

All conditions are identical to example 8 except that 60 g of catalyst was dissolved in the glycerol layer prior to the reaction. The reaction proceeded to completion in 3 hours as in example 2.

What is claimed is:

1. A process for producing conjugated linoleic acid or salts thereof from a material rich in linoleate moieties comprising; mixing said material with a waste alkaline glycerol derived from alkali transesterification of triglycerides, heating to a temperature above 170° C., cooling and separating said conjugated linoleic acid by the addition of at least one of the group consisting of a salt, a salt solution and an acid.

2. A process as claimed in claim 1, wherein said material is a vegetable oil rich in linoleic acid.

3. A process as claimed in claim 1, wherein said material is selected from the group consisting of soapstock, triglycerides, fatty acids, soaps, phospholipids and esters rich in linoleate moieties.

4. A process, as claimed in claim 1, wherein said transesterification is carried out in the presence of an alkali selected from the group consisting of sodium metal, sodium hydroxide, sodium alkoxylate, potassium metal, potassium hydroxide and potassium alkoxylate.

5. A process, as claimed in claim 1, wherein said linoleate rich material is derived from an oil selected from the group consisting of cottonseed, cucumber, grapeseed, corn, flax, safflower, soybean, sunflower, and walnut oils.

6. A process, as claimed in claim 1, including the step of including additional alkali with the reaction mixture to augment the reaction.

7. A process according to claim 6 where the additional alkali is selected from the group consisting of sodium metal, sodium hydroxide, sodium alkoxylate, sodium carbonate, potassium metal, potassium hydroxide, potassium carbonate, calcium hydroxide, calcium oxide and potassium alkoxylate.

8. A process, as claimed in claim 2, including the step including additional alkali with the reaction mixture to augment the reaction.

9. A process according to claim 8 where the additional alkali is selected from the group consisting of sodium metal, sodium hydroxide, sodium alkoxylate, sodium carbonate, potassium metal, potassium hydroxide, potassium carbonate, calcium hydroxide, calcium oxide and potassium alkoxylate.

10. A process, as claimed in claim 6, wherein a mixture of two said alkalis is used to catalyse conversion of linoleate soaps to conjugated linoleate soaps.

11. A process, as claimed in claim 8, wherein a mixture of two said alkalis is used to catalyse conversion of the linoleate soaps to conjugated linoleate soaps.

12. A process, as claimed in claim 10, wherein said alkalis are selected from the group consisting of potassium hydroxide, sodium hydroxide, potassium carbonate, sodium carbonate, calcium hydroxide and calcium oxide.

13. A process, as claimed in claim 11, wherein said alkalis are selected from the group consisting of potassium hydroxide, sodium hydroxide, potassium carbonate, sodium carbonate, calcium hydroxide and calcium oxide.

14. A process, as claimed in claim 1, where said acid is selected from the group consisting of hydrochloric, sulfuric, phosphoric and citric acid.

15. A process as claimed in claim 1, where the reaction mixture is acidified and separated into two phases by the addition of tannin or condensed tannin.

16. A process as claimed in claim 1, where the reaction mixture is acidified and separated into two phases by the addition of polyethylene glycol with a molecular weight greater than 106 Daltons.

17. A process, as claimed in claim 1, where the reaction mixture is acidified and separated into two phases by the addition of a monohydric alcohol.

18. A process, as claimed in claim 15, wherein said monohydric alcohol is selected from the group consisting of methanol, ethanol, butanol, isoproponal, and n-propanol.

19. A process, as claimed in claim 2, wherein said salt is a monovalent cationic salt selected from the group consisting of sodium, potassium, lithium and caesium salts.

20. A process, as claimed in claim 2, wherein said salt is a polyvalent cationic salt selected from the group consisting of calcium, magnesium, zinc, copper, aluminum, iron, and chromium salts.

* * * * *